US009866953B2

(12) United States Patent
Chong et al.

(10) Patent No.: US 9,866,953 B2
(45) Date of Patent: Jan. 9, 2018

(54) ELECTRONIC STETHOSCOPE

(71) Applicant: CliniCloud Inc., San Francisco, CA (US)

(72) Inventors: Hon Weng Chong, Toorak (AU); Lain Cai Cai, Macleod (AU); An Lin, Eight Mile Plains (AU); Robert James Skillington, Glen Iris (AU)

(73) Assignee: CLINICLOUD INC., San Francisco, CA (US)

( * ) Notice: Subject to any disclaimer, the term of this patent is extended or adjusted under 35 U.S.C. 154(b) by 262 days.

(21) Appl. No.: 14/591,847

(22) Filed: Jan. 7, 2015

(65) Prior Publication Data

US 2015/0190110 A1  Jul. 9, 2015

Related U.S. Application Data

(60) Provisional application No. 61/925,083, filed on Jan. 8, 2014.

(51) Int. Cl.
*A61B 7/04* (2006.01)
*H04R 1/46* (2006.01)
*A61B 5/00* (2006.01)
*A61B 5/024* (2006.01)

(52) U.S. Cl.
CPC ............. *H04R 1/46* (2013.01); *A61B 7/04* (2013.01); *A61B 5/02444* (2013.01); *A61B 5/6898* (2013.01); *H04R 2420/09* (2013.01)

(58) Field of Classification Search
CPC ...................................... H04R 1/46
See application file for complete search history.

(56) References Cited

U.S. PATENT DOCUMENTS

| | | | | |
|---|---|---|---|---|
| 2003/0002685 A1* | 1/2003 | Werblud | .......... | A61B 7/04 381/67 |
| 2004/0109571 A1* | 6/2004 | Yoshimine | .......... | A61B 5/00 381/67 |
| 2005/0157887 A1* | 7/2005 | Kim | .......... | A61B 7/04 381/67 |
| 2006/0098825 A1* | 5/2006 | Katz | .......... | A61B 7/04 381/67 |
| 2008/0146276 A1* | 6/2008 | Lee | .......... | A61B 5/6887 455/556.1 |
| 2008/0232604 A1* | 9/2008 | Dufresne | .......... | A61B 5/061 381/67 |
| 2011/0087135 A1* | 4/2011 | Ferzli | .......... | A61B 7/04 600/586 |
| 2011/0096936 A1* | 4/2011 | Gass | .......... | A61B 7/04 381/67 |
| 2014/0163422 A1* | 6/2014 | Poplaw | .......... | H04M 1/026 600/586 |

* cited by examiner

*Primary Examiner* — Carl H Layno
*Assistant Examiner* — Jennifer Ghand
(74) *Attorney, Agent, or Firm* — Lowenstein Sandler LLP

(57) ABSTRACT

An electronic stethoscope has a body with a diaphragm at one end of the body. A microphone is housed within the body, wherein the microphone is to generate a first analog audio signal based on sounds waves amplified by the diaphragm. A processing device is also housed within the body and connected to the microphone. The processing device is to receive a second audio signal from a computing device connected to the electronic stethoscope via a connection, and enable the microphone responsive to receipt of the second audio signal.

12 Claims, 12 Drawing Sheets

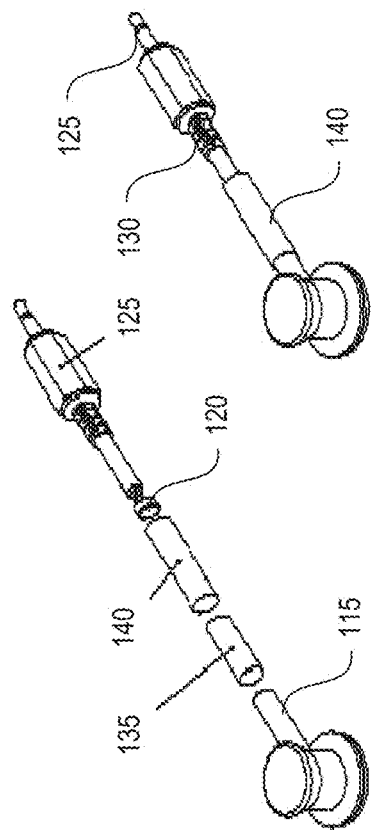
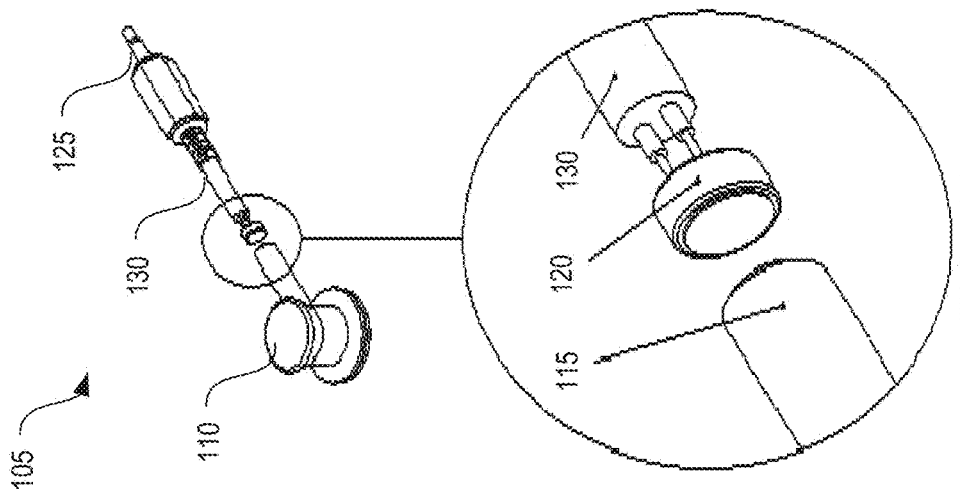

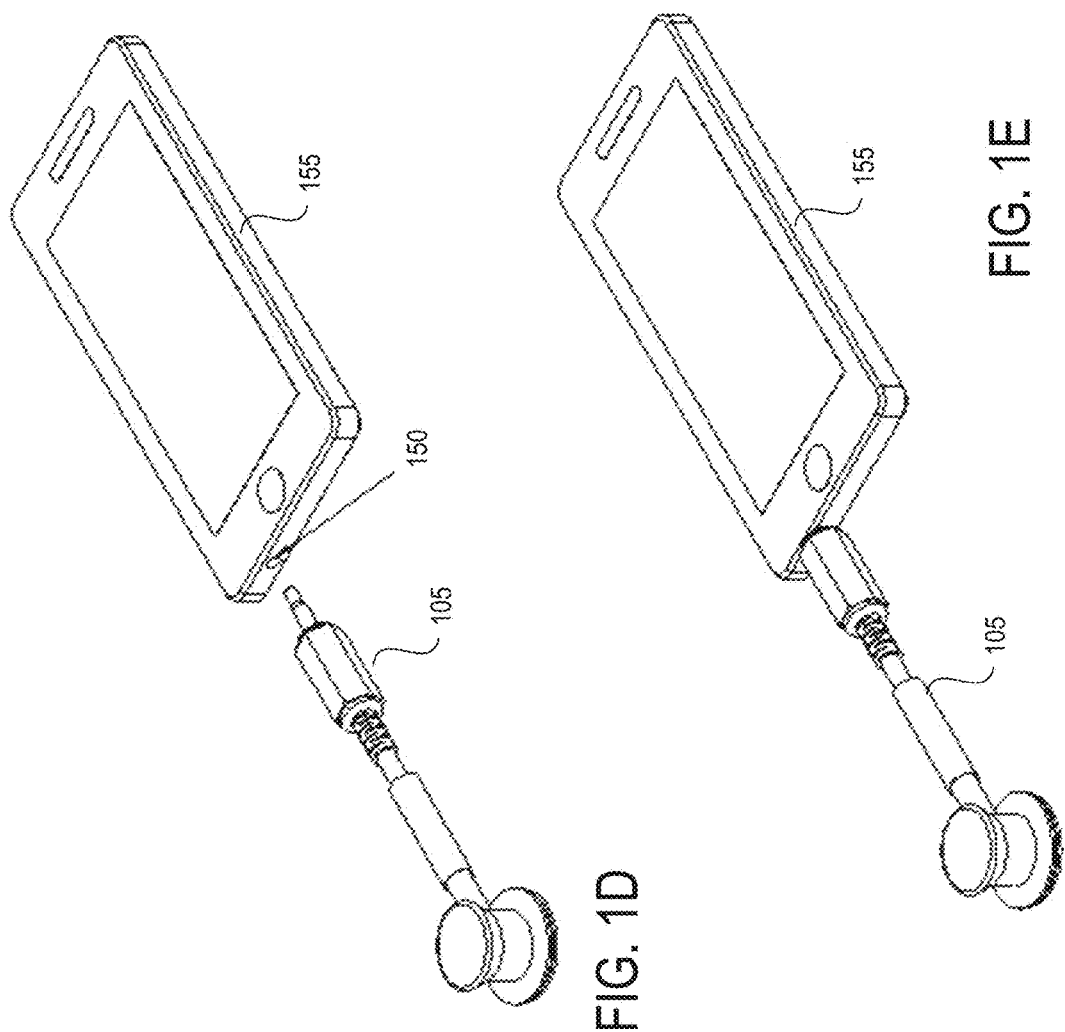

ELECTRONIC STETHOSCOPE

RELATED APPLICATIONS

This patent application claims the benefit under 35 U.S.C. §119(e) of U.S. Provisional Application No. 61/925,083, filed Jan. 8, 2014, which is herein incorporated by reference.

BACKGROUND OF THE INVENTION

Conventional stethoscopes are acoustic medical devices for auscultation (listening to the internal sounds of the body). To interpret the sounds picked up by a conventional stethoscope typically requires training. Accordingly, stethoscopes are traditionally used by medical professionals to aid in diagnosis of patients. However, it can be difficult for lay persons to properly use stethoscopes. Additionally, current delivery room practices are not consistently accurate for the monitoring of the newborn heart rate.

BRIEF DESCRIPTION OF THE DRAWINGS

The embodiments described herein will be understood more fully from the detailed description given below and from the accompanying drawings, which, however, should not be taken to limit the application to the specific embodiments, but are for explanation and understanding only.

FIGS. 1A-1B are exploded views of an electronic stethoscope attachment for mobile phones and other computing devices, in accordance with one embodiment.

FIG. 1C is a perspective view of the electronic stethoscope attachment of FIGS. 1A-1B, in accordance with one embodiment.

FIG. 1D is a perspective view of the electronic stethoscope attachment of FIGS. 1A-1C near a mobile phone, in accordance with one embodiment.

FIG. 1E is a perspective view of the electronic stethoscope attachment of FIGS. 1A-1D after it has been plugged into the mobile phone, in accordance with one embodiment.

DETAILED DESCRIPTION OF THE PRESENT INVENTION

Figure 2:
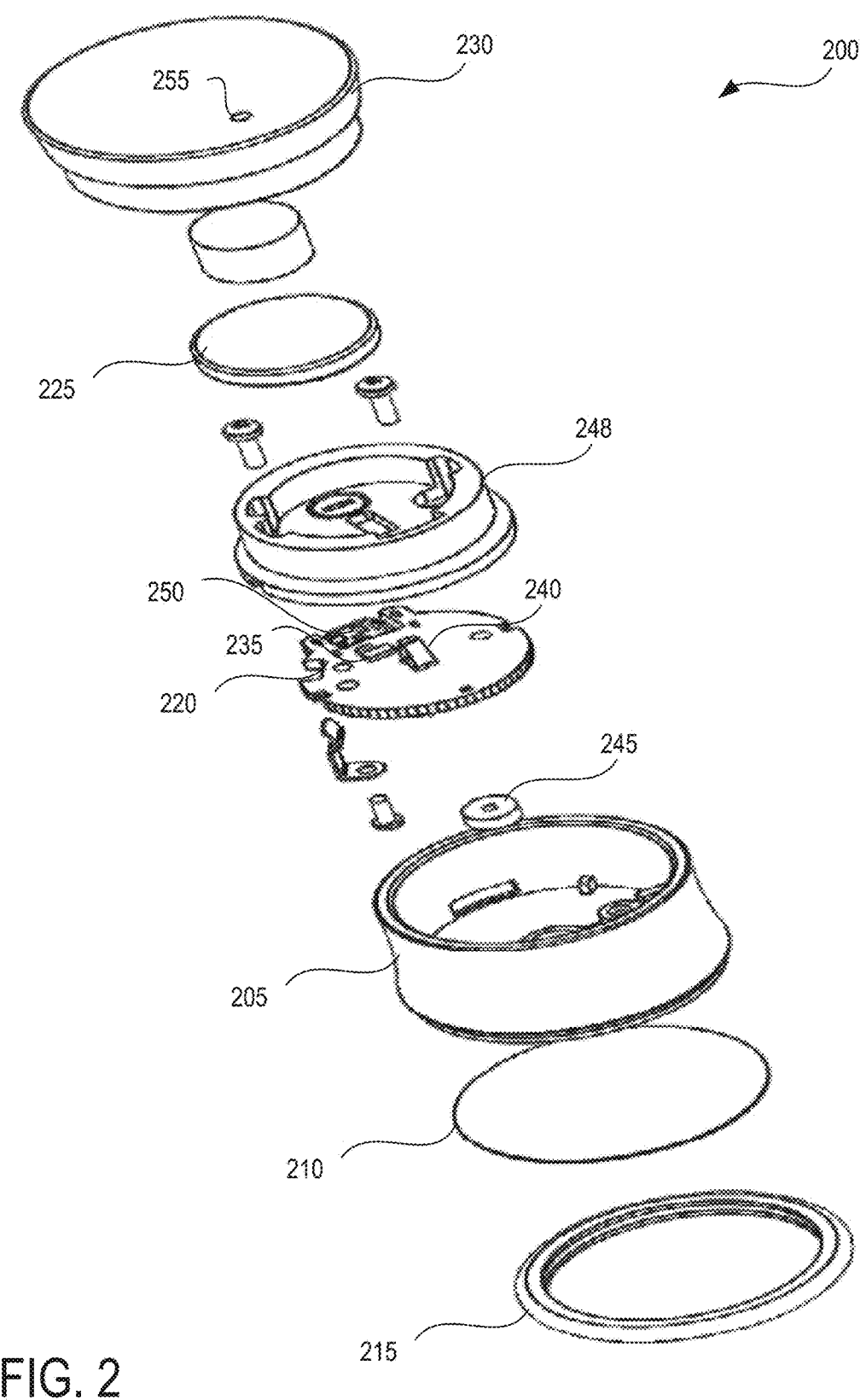
FIG. 2 is an exploded view of an electronic stethoscope, in accordance with one embodiment.

Described herein are embodiments of an electronic stethoscope that pairs to a user device and of a stethoscope module that runs on the user device. The electronic stethoscope may be connected to the user device via a wired or wireless connection, and may activate, deactivate, and generate diagnostic audio signals based on signals (e.g., audio signals) received from the user device over the connection. The electronic stethoscope may not include any buttons, such as for turning on or off the electronic stethoscope or for taking measurements. Instead, the electronic stethoscope may rely on signals from the user device to perform such operations.

The user device may include a stethoscope module (e.g., a stethoscope application or "app") that enables the user device to communicate with the electronic stethoscope and cause the electronic stethoscope to operate. The stethoscope module may include sub-modules for processing diagnostic audio data and determining medical information such as adult heart beat information, child heart beat information, neonate heart beat information, adult breathing information, child breathing information and/or neonate breathing information. The stethoscope module may guide a user through the placement and use of the electronic stethoscope (e.g., via a series of prompts of a user interface), and may process received diagnostic audio data to determine the medical information. This medical information may assist lay persons and/or physicians in patient diagnosis.

The electronic stethoscope may plug into a 4-pole audio port, a universal serial bus (USB) port (e.g., a micro-USB port) or a Lightning™ port of a user device on which the stethoscope module is installed. A stethoscope head of the electronic stethoscope may be placed against the chest of a patient (e.g., a neonate), back of a patient, or other region of a patient. The electronic stethoscope may transmit an analog audio signal to the user device through the 4-pole audio port, and the user device may convert the analog audio signal into a digital audio signal. The electronic stethoscope may alternatively generate a digital audio signal that may be transmitted to the user device through, for example, the micro-USB or Lightning port. The heart rate monitor module may then process the digital audio signal to determine medical information such as a heart rate of the patient, breathing information about the patient, etc., and may output the medical information with a visual and/or audio indicator via a user interface.

The stethoscope module described in embodiments may provide an accurate heart rate for a neonate, a child, a young adult, an elderly adult, and so on. The stethoscope module may also provide accurate breathing information and determine conditions such as air or fluid in a patient's lungs, increased thickness of a chest wall, over-inflation of a part of the lungs, reduced airflow in a part of the lungs, and so on. The heart rate information and/or breathing information may help a medical practitioner to diagnose a patient and/or may help a patient determine when they should visit a doctor.

When used to measure the heart rate of a neonate, the stethoscope module may enable a medical practitioner to evaluate whether resuscitation of the neonate should be performed. For example, the American Heart Associate provides guidelines detailing the analysis for a medical practitioner to perform during a neonatal resuscitation. Heart rate is used at various stages of the analysis. Accordingly, it is important for a medical practitioner to accurately determine a neonate's heart rate. However, traditional techniques for determining a neonate's heart rate during the first few minutes of life are often inaccurate or cumbersome.

Embodiments provide a low cost accurate system for determining medical information such as the heart rate and/or breathing information of a neonate and of other patients. In the use case of monitoring a neonate, the heart rate of the neonate may be accurately determined in embodiments just moments after a mother gives birth. Such heart rate measurements may be made without any special preparation simply by placing the stethoscope head of the electronic stethoscope against the chest of a newborn.

In some embodiments, an electronic stethoscope with no or minimal active components may provide an unprocessed audio signal to a user device. A stethoscope module running on the user device may then use the analog to digital converters and processing power of the user device to process the analog signal. Accordingly, a stethoscope system described in embodiments may leverage the existing capabilities of user devices such as mobile phones, coupled with a low cost electronic stethoscope (e.g., an analog electronic stethoscope attachment), to provide a lower cost and more accurate alternative to many traditional systems.

FIGS. 1A-1B are exploded views of an electronic stethoscope attachment 105 for mobile phones and other computing devices, in accordance with one embodiment. FIG. 1C is a perspective view of the electronic stethoscope attachment 105. The electronic stethoscope attachment 105 includes a stethoscope head 110 having a stethoscope head barrel 115 coupled thereto. In one embodiment, the stethoscope head 110 has a metal body with a flexible plastic diaphragm therein.

A microphone 120 may be disposed within an end of the barrel 115. In one embodiment, the microphone 120 is a noise-cancelling microphone and/or an electret microphone. In one embodiment, the microphone 120 is a microelectromechanical systems (MEMS) microphone. The microphone 120 may be used to produce an electrical response representing the sound of heartbeats, breathing, or other noise transmitted through the stethoscope head 110.

The microphone 120 may be electrically coupled to a 4-pole audio jack 125 (e.g., a 3.5 mm audio plug known as a tip-ring-ring-sleeve (TRRS)) via a cable 130. The cable 130, microphone 120 and barrel 115 may be encased within a tubing such as heat shrink tubing. As shown, in one embodiment an inner layer 135 and outer layer 140 of heat shrink tubing are used to encase and mechanically couple the barrel 115, microphone 120 and cable 130. The tubing may also insulate the microphone 120 from environmental noise and limit received sound waves to the sound waves captured by the stethoscope head 110. As shown, in one embodiment the electronic stethoscope attachment 105 does not include any power source. Instead, the electronic stethoscope attachment 105 may be passively powered through the 4-pole audio jack 125. Alternatively, the electronic stethoscope attachment 105 may include an active power source such as a battery.

FIG. 1D is a perspective view of the electronic stethoscope attachment 105 of FIGS. 1A-1C near a mobile phone 155, in accordance with one embodiment. FIG. 1E is a perspective view of the electronic stethoscope attachment 105 of FIGS. 1A-1D after it has been plugged into the mobile phone 155, in accordance with one embodiment. As shown, the electronic stethoscope attachment 105 connects to the mobile phone 155 via a 4-pole stereo port 150 in one embodiment. However, the electronic stethoscope attachment 105 may alternatively couple to the mobile phone 155 via a universal serial bus (USB) port. For example, an analog to digital converter may plug into a USB port on the mobile phone, and the electronic stethoscope attachment 105 may plug into the analog to digital converter. Alternatively, the electronic stethoscope attachment 105 may include a USB module that converts the analog audio signal into a digital audio signal that can be transmitted to the mobile phone 155 via a USB port. The electronic stethoscope attachment 105 may additionally or alternatively include a Wi-Fi® module, a Zigbee® module, a Bluetooth® module or other wireless module that enables the electronic stethoscope attachment 105 to transmit an audio signal wirelessly to the mobile phone 155. Such a wireless module may receive an analog audio signal from the microphone 120, convert the analog audio signal to a digital audio signal, format the digital audio signal in accordance with a wireless protocol (e.g., Wi-Fi, Zigbee, Bluetooth, etc.), and then transmit the digital audio signal to the mobile phone 155. Alternatively, the electronic stethoscope attachment 105 may include an analog to digital converter that converts the audio signal from an analog audio signal to a digital audio signal before sending the audio signal to the wireless module. Note that in alternative embodiments other types of user devices such as tablet computers, laptop computers, desktop computers, and so on may connect to the electronic stethoscope attachment rather than a mobile phone.

FIG. 2 is an exploded view of an electronic stethoscope 200, in accordance with one embodiment. The electronic stethoscope 200 includes a body 205 and a diaphragm 210 disposed at a bottom of the body 205. The body may be stainless steel, aluminum, graphite, plastic, or a combination thereof. Other materials may also be used for the body.

The diaphragm 210 may be a flat or cupped diaphragm. The diaphragm 210 may be a rigid or flexible disk, and may be made of an epoxy-fiberglass compound (e.g., Bakelite), plastic (e.g., polyethylene), or other material. A ring 215 may be attached to the bottom of the body 205 and/or to the diaphragm. The ring 215 (sometimes referred to as an anti-chill ring) may improve patient comfort, and may enable better suction, thus improving sound quality. The ring 215 may be silicone rubber, polyvinyl chloride, or another material.

The bottom of the body 205 may have a hole. A gasket 245 may be placed in the hole. The gasket 245 may be made from urethane, rubber or other materials, and may have a small inner diameter channel through which acoustic pressure waves generated by the diaphragm 210 travel. The gasket 245 may provide acoustic insulation from environmental noise and limit received sound waves to the sound waves captured by the diaphragm 210.

A printed circuit board (PCB) 220 may be disposed within the body 205. The printed circuit board (PCB) 220 may include a microphone 240 that is positioned at one end of the gasket 245 to pick up the acoustic pressure waves transmitted through the channel. The microphone 240 may be a noise-cancelling microphone and/or an electret microphone. In one embodiment, the microphone 240 is a MEMS microphone. The microphone 120 may be used to produce an electrical response representing the sound of heartbeats, breathing, or other noise transmitted through the channel. The electrical response produced by the microphone may be an analog audio signal.

The PCB 220 further includes a processing device 235. Processing device 235 may be one or more general-purpose processors such as a microprocessor, central processing unit, or the like. The term "processing device" is used herein to refer to any combination of one or more integrated circuits and/or packages that include one or more processors (e.g., one or more processor cores). The processing device may include a complex instruction set computing (CISC) microprocessor, reduced instruction set computing (RISC) microprocessor, very long instruction word (VLIW) microprocessor, processor implementing other instruction sets, or processors implementing a combination of instruction sets. The processing device 235 may also be one or more special-purpose processing devices such as an application specific integrated circuit (ASIC), a field programmable gate array (FPGA), a digital signal processor (DSP), network processor, or the like. In one embodiment, the processing device 235 is a system on a chip (SoC) including a processor, a memory, and one or more internal ports. In one embodiment, the processing device is an ARM® processing device.

The PCB 220 may further include a port 250 usable to connect the electronic stethoscope to a cable. In one embodiment, the port 250 is a universal serial bus (USB) port, such as a standard USB port, a micro-USB port, or a mini-USB port. Alternatively, the port 250 may be a 3.5 mm audio jack, a Lightning port or other type of port. The microphone 240 may output audio signals to the port for transmission over an electrical cable and to a user device such as a mobile phone, tablet computer, etc. The processing device 235 may additionally connect to the port 250, and may receive incoming audio signals from the user device via the port 250. The port 250 may be used to transmit digital signals and/or analog signal from processing device 235, and may further be used to receive digital signals and/or analog signals.

Processing device 235 may manage a power state of itself and of the rest of the electronic stethoscope 200. In one embodiment, processing device 235 determines when to power on and off the microphone 240, and activates and deactivates the microphone 240 accordingly. In one embodiment, processing device 235 maintains the microphone 240 in an off state. When the processing device 235 receives an audio signal from the port 250 (e.g., a digital audio signal or an analog audio signal), processing device 235 processes the audio signal to determine whether that audio signal is an audio signature that matches a stored audio signature. If the received audio signal is an audio signature matching a stored audio signature, the processing device 235 powers on (activates) the microphone 240 and connects the microphone 240 to the port 250. Processing device 235 may also power on the microphone 240 when it receives a digital unlock signature that matches a stored digital unlock signature or that can be verified. The digital unlock signature may or may not be an audio signal. In one embodiment, the digital unlock signature is a signature generated using any conventional electronic authentication techniques. For example, the digital unlock signature may be a signature generated by a stethoscope module based on use of a security token. The microphone 240 then begins generating a diagnostic audio signal (e.g., an analog diagnostic audio signal) and sending the diagnostic audio signal through the port 250.

The processing device 235 may continuously or periodically receive an audio signature via the port 250. If the processing device 235 fails to receive the audio signature for a threshold amount of time, then the processing device 235 may deactivate the microphone 240 and/or disconnect the microphone 240 from the port 250. Thus, the processing device 235 may begin taking measurements and stop taking measurements based on audio signals received from a user device, rather than based on a user pressing any button on the electronic stethoscope 200. Accordingly, the electronic stethoscope 200 may not include any physical buttons in embodiments.

In one embodiment, processing device 235 places itself into a low power or standby state if the microphone has been powered off for a threshold amount of time. While the processing device is in the low power state, minimal power may be consumed. This may prolong a battery life of the electronic stethoscope. The processing device monitors the port 250 for an audio wake-up signal while in the low power state. Responsive to receipt of such an audio wake-up signal, processing device 250 transitions out of the low power state into a higher power state (e.g., into a full power state). Alternatively, and/or additionally, electronic stethoscope 200 may include a power switch that powers on and off the processing device 235.

In one embodiment, electronic stethoscope 200 includes a housing 248 that the PCB 220 may be mounted to. The housing 248 may additionally hold a battery 225, which may be a coin slot battery or other type of battery. The battery 225 may be a rechargeable battery or a disposable battery. The electronic stethoscope 200 may additionally include a lid 230 that secures to a top of the body 205 such that the battery 225, housing 248, PCB 220 and other components are enclosed within the body 205.

In one embodiment, the lid 230 includes an indicator light 255, which may be a light emitting diode (LED) or other type of light. The indicator light 255 may indicate whether the electronic stethoscope 200 is active, whether it is generating diagnostic audio signals, etc. Such indications may be provided via a continuous light or blinking light pattern.

Figure 3:
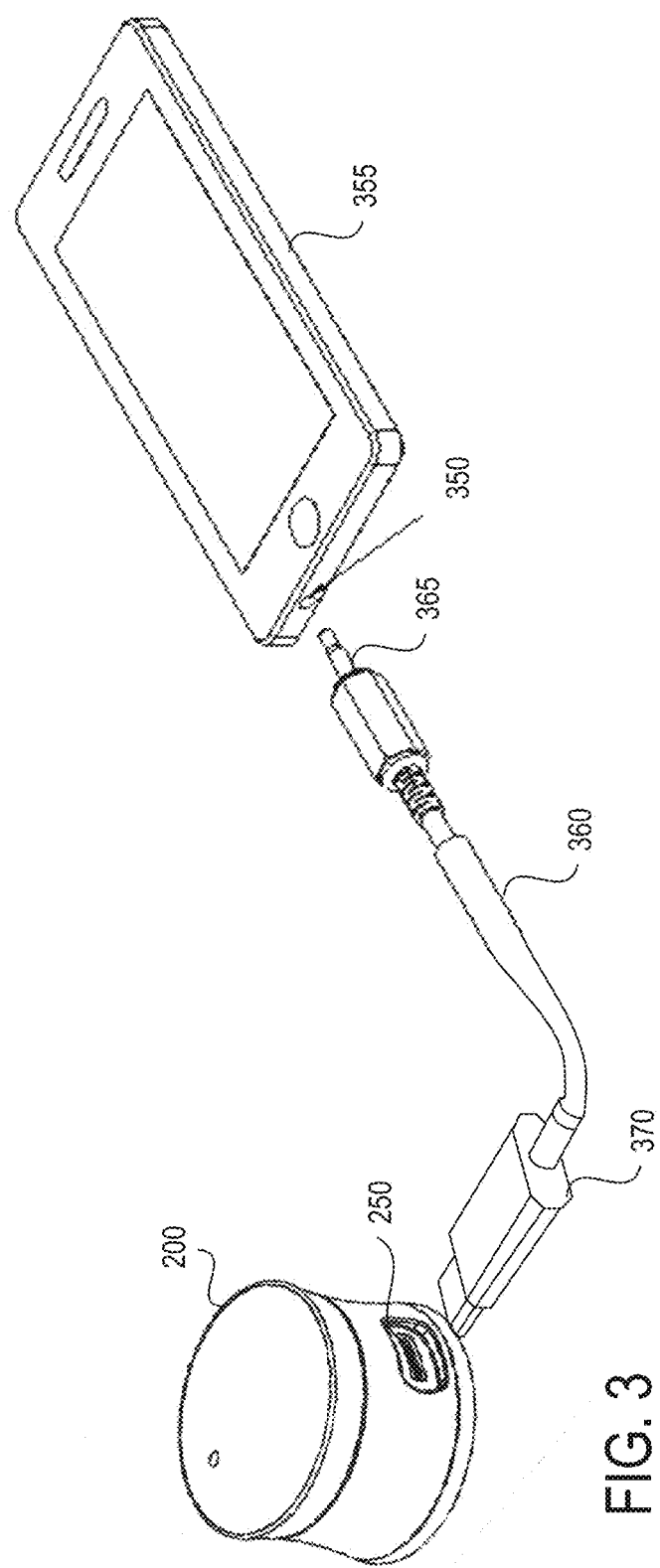
FIG. 3 is a perspective view of the electronic stethoscope of FIG. 2 that is to be connected to a mobile phone by a cable, in accordance with one embodiment.

FIG. 3 is a perspective view of the electronic stethoscope 200 of FIG. 2 that is to be connected to a mobile phone 355 by a cable 360, in accordance with one embodiment. As shown, the electronic stethoscope 200 includes a USB port 250 (e.g., a micro-USB port). However, the electronic stethoscope may alternatively include a 4-pole stereo port, a Firewire® port, a Lightning™ port, a Thunderbolt™ port, or other port.

In one embodiment, the electronic stethoscope 200 outputs an analog audio signal and/or receives an analog audio signal through the port 250. This may be true even in cases where the port 250 is a USB port or other port that is traditionally used for the transmission of digital signals. In such a case the conventionally digital port (e.g., USB port) is repurposed for the transmission of the analog audio signal. For example, a micro-USB port has five pins. In one embodiment, a third pin (D+ pin) of the micro-USB port is assigned for a right audio channel, a fifth pin (ground or GND pin) is assigned to ground, and a second pin (D− pin) is assigned for a microphone channel. Thus, the micro-USB port (or other USB port) may be used to send an audio signal to mobile phone 355 through a stereo audio port 350 of a mobile phone 355 and to receive an audio signal from the mobile phone 355 via the stereo audio port 350 of the mobile phone 355.

In one embodiment, the cable 360 has different connector types at its two ends. For example, in the illustrated embodiment the cable 360 has a micro-USB connector 370 at a first end that plugs into the port 250 of the electronic stethoscope 200 and a 3.5 mm audio jack 365 that plugs into the 4-pole stereo port 350 of the mobile phone 355. The five pins of the micro-USB connector 370 may be wired to the four poles of the 3.5 mm audio jack 365 such that a right (R) pole of the audio jack 365 is connected to a D+ wire of the micro-USB connector 370, a ground of the 3.5 mm audio jack 365 is connected to a ground of the micro-USB connector 370, and a microphone (MIC) pole of the 3.5 mm audio jack 365 is connected to a D− pin of the micro-USB connector 370.

As shown, the cable 360 connects to the mobile phone 355 via a 4-pole stereo port 350 in one embodiment. Using the 4-pole stereo port 350 of the mobile phone for connecting to the electronic stethoscope 200 has numerous advantages. In particular, the mobile phone 350 includes analog to digital converts and/or digital to analog converts coupled to the 4-pole stereo jack 350 and is optimized for the processing of audio signals received from the 4-pole stereo jack 350. Thus, the native capabilities of the mobile phone 355 for processing analog audio signals received via the 4-pole audio jack 250 may be utilized.

However, the cable 360 may alternatively couple to the mobile phone 355 via a universal serial bus (USB) port in the mobile phone 355. For example, an analog to digital converter may plug into a USB port on the mobile phone 355, and the cable 360 may plug into the analog to digital converter. Alternatively, the electronic stethoscope 200 may include a USB module that converts the analog audio signal into a digital audio signal that can be transmitted to the mobile phone 355 via a USB port.

The electronic stethoscope attachment 200 may additionally or alternatively include a Wi-Fi® module, a Zigbee® module, a Bluetooth® module or other wireless module that enables the electronic stethoscope attachment 315 to transmit an audio signal wirelessly to the mobile phone 355. Such a wireless module may receive an analog audio signal from the microphone 240, convert the analog audio signal to a digital audio signal, format the digital audio signal in accordance with a wireless protocol (e.g., Wi-Fi, Zigbee, Bluetooth, etc.), and then transmit the digital audio signal to the mobile phone 355. Alternatively, the electronic stethoscope 355 may include an analog to digital converter that converts the audio signal from an analog audio signal to a digital audio signal before sending the audio signal to the wireless module. Note that in alternative embodiments other types of user devices such as tablet computers, laptop computers, desktop computers, and so on may connect to the electronic stethoscope attachment rather than a mobile phone.

Figure 4:
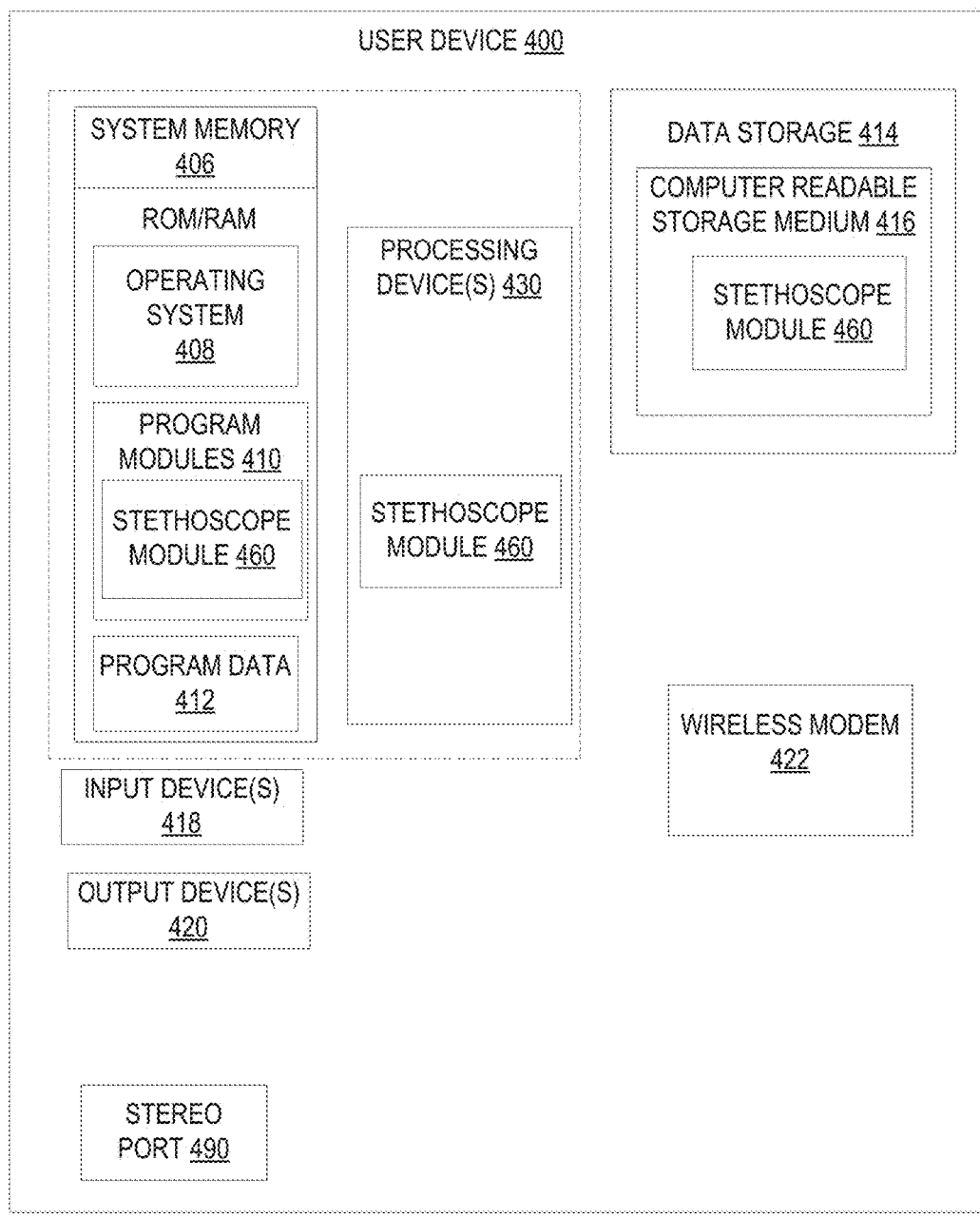
FIG. 4 is a block diagram illustrating an exemplary user device having a heart rate monitor module installed thereon, in accordance with one embodiment.

FIG. 4 is a block diagram illustrating an exemplary user device 400 that includes a stethoscope module 460 installed thereon. The user device 400 may be any type of computing device such as an electronic book reader, a personal digital assistant (PDA), a mobile phone, a laptop computer, a portable media player, a tablet computer, a camera, a video camera, a netbook, a desktop computer, a gaming console, and the like. In one embodiment, the user device 400 corresponds to mobile phone 155 of FIGS. 1D-1E and to mobile phone 355 of FIG. 3.

The user device 400 includes one or more processing devices 430, such as one or more central processing units (CPUs), microcontrollers, field programmable gate arrays (FPGAs), digital signal processors (DSP)s, and/or other types of processors. The user device 400 also includes system memory 406, which may correspond to any combination of volatile and/or non-volatile storage mechanisms. The system memory 406 stores information which provides an operating system component 408, various program modules 410 such as stethoscope module 460, program data 412, and/or other components. The user device 400 performs functions by using the processing device(s) 430 to execute instructions provided by the system memory 406.

The user device 400 also includes a data storage device 414 that may be composed of one or more types of removable storage and/or one or more types of non-removable storage. The data storage device 414 includes a non-transitory computer-readable storage medium 416 on which is stored one or more sets of instructions embodying any one or more of the methodologies or functions described herein. As shown, instructions for the stethoscope module 460 may reside, completely or at least partially, within the computer readable storage medium 416, system memory 406 and/or within the processing device(s) 430 during execution thereof by the user device 400, the system memory 406 and the processing device(s) 430 also constituting computer-readable media. The user device 400 may also include one or more input devices 418 (keyboard, mouse device, touchpad, touchscreen, specialized selection keys, etc.) and one or more output devices 420 (displays, printers, audio output mechanisms, tactile feedback mechanisms (e.g., vibrators) etc.).

The user device 400 may further include a wireless modem 422 to allow the user device 400 to communicate via a wireless network (e.g., such as a Wi-Fi network or a wireless network provided by a wireless carrier) with other computing devices, such as remote computers, a cloud-based medical diagnostic service, and so forth. The wireless modem 422 may allow the user device 400 to handle both voice and non-voice communications (such as communications for text messages, multimedia messages, media downloads, web browsing, etc.).

The processing device(s) 430 may include at least one digital signal processor (DSP) that includes an analog to digital conversion capability. The user device may include a stereo port 490 (e.g., a 4-pole stereo port) through which an analog audio signal may be received. The DSP may convert the received analog audio signal into a digital audio signal. The stethoscope module 460 may then process the digital audio signal to, for example, determine a heart rate of a patient, determine breathing information of the patient, and so on.

Figure 5:
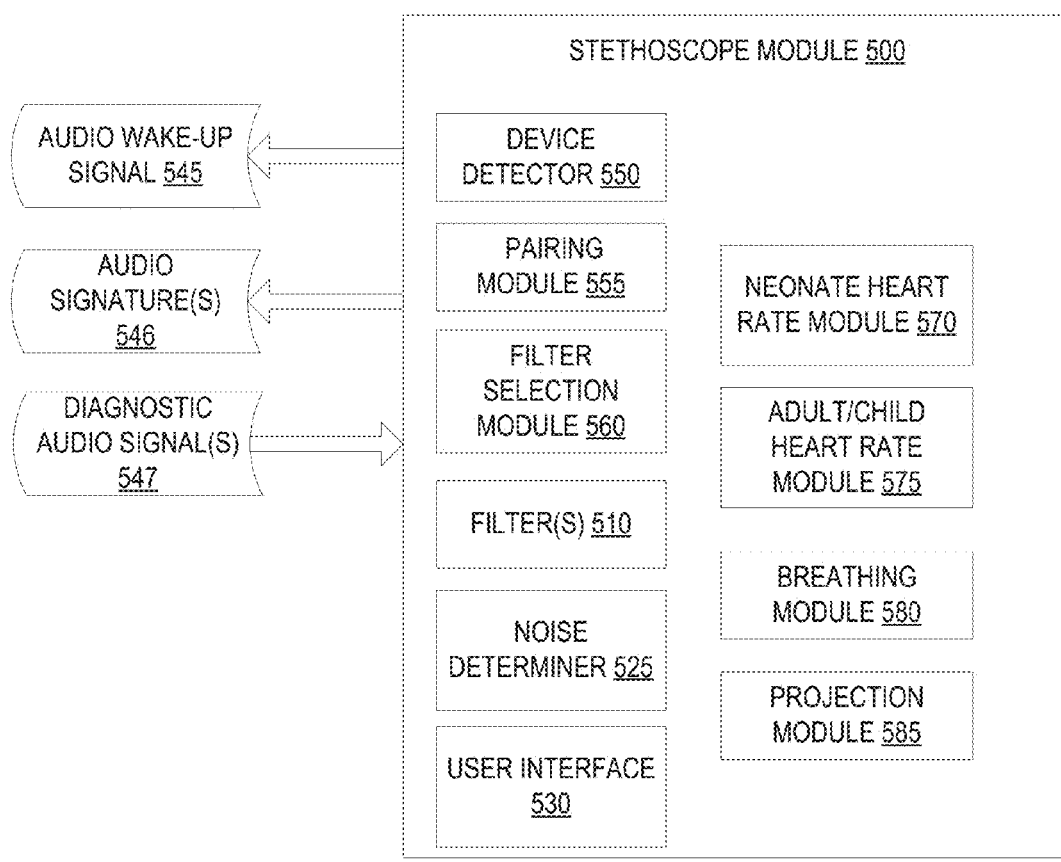
FIG. 5 is a block diagram of a stethoscope module, in accordance with one embodiment.

FIG. 5 is a block diagram of one embodiment of a stethoscope module 500, which may correspond to the stethoscope module 460 of FIG. 4. The stethoscope module 500 may be implemented in software, firmware, hardware, or a combination thereof. In one embodiment, the stethoscope module 500 includes one or more filters 510, a noise determiner 525, a user interface 530, a device detector 550, a pairing module 555 and/or a filter selection module 560. Stethoscope module 500 may additionally include a neonate heart rate module 570, an adult/child heart rate module 575 and/or a breathing module 580. The functionality of one of more of these components may also be combined into a single module or divided into multiple modules.

Device detector 550 may detect when a user device on which stethoscope module 500 runs is connected to an electronic stethoscope, such as electronic stethoscope attachment 105 of FIGS. 1A-1E or electronic stethoscope 200 of FIGS. 2-3. Device detector 550 may listen for a device identification signal generated by electronic stethoscope 200 to identify the nature of the connected device. Responsive to device detector 550 initially detecting the electronic stethoscope or another connected device, pairing module 555 may generate an audio wake-up signal 545, which is then sent to the electronic stethoscope or other connected device. The audio wake-up signal 545 may be a particular tone that the electronic stethoscope listens for while it is in a standby state. Responsive to receipt of the audio wake-up signal 545, the electronic stethoscope may transition to a higher power state to enable it to begin processing additional signals from the stethoscope module 500.

After sending the audio wake-up signal 545, pairing module 555 generates an audio signature 546, which is then sent to the electronic stethoscope. The audio signature may have a frequency anywhere from about 2 kHz to about 10 kHz in embodiments. Alternatively, other frequencies may be used. The audio signature 546 is used to authenticate the stethoscope module 500 to the electronic stethoscope. The electronic stethoscope processes the audio signature 546 for authentication purposes, and then determines whether or not to communicate with the stethoscope module based on a result of the authentication. If the audio signature does not meet certain criteria (e.g., does not match an audio signature stored by the electronic stethoscope), then the electronic stethoscope will not send diagnostic audio signals to stethoscope module 500. If the audio signature does meet the criteria, then the electronic stethoscope will begin generating diagnostic audio signals 547 and providing those diagnostic audio signals to the user device on which stethoscope module 500 is running.

In one embodiment, pairing module 555 continuously or periodically resends the audio signature 546 to the electronic stethoscope. For example, pairing module 555 may send the audio signature to the electronic stethoscope every 0.5 seconds, every second, every 10 seconds, every minute, or at some other interval. If pairing module 555 fails to send an audio signature expected by the electronic stethoscope, then the electronic stethoscope may stop sending diagnostic audio signals 547. If no diagnostic audio signals 547 or other audio signals are received from the electronic stethoscope for a threshold amount of time (e.g., 1 second, 2 seconds, 5 seconds, etc.), then pairing module may determine that a connection to the electronic stethoscope has been lost. Pairing module 555 may then cause user interface 530 to output a "no signal," "device disconnected," "reconnect device" or other similar message to alert a user of the lost connection.

One way or two way authentication may be performed between the electronic stethoscope and the stethoscope module 500 using audio signatures. For example, in addition to pairing module 555 sending audio signature 546 to the electronic stethoscope, the electronic stethoscope may send another audio signature that pairing module 555 may analyze to authenticate the electronic stethoscope to the stethoscope module 500. Authentication may be performed by processing the received audio signature (e.g., by performing a fast Fourier transform), and then comparing a computed representation of the received audio signature to a representation of a particular audio signature. The particular audio signature may be stored and/or the representation of the particular audio signature may be stored. If the representation of the particular audio signature matches the representation of the received audio signature, then authentication is successful. Otherwise authentication fails.

In one embodiment, each installation of a stethoscope module 500 has its own unique audio signature, and each electronic stethoscope has its own audio signature. Alternatively, the same audio signature may be used by multiple electronic stethoscopes and/or stethoscope modules. If unique audio signatures are used, then each electronic stethoscope may include a library of acceptable audio signatures and/or may include an algorithm that may be used to process a received audio signature to determine if that audio signature has properties that satisfy authentication criteria. The stethoscope module 500 may likewise have a library of audio signatures and/or algorithm for determining whether properties of an audio signature satisfy authentication criteria in some embodiments.

Once stethoscope module 500 is paired to an electronic stethoscope, stethoscope module 500 may receive one or more diagnostic audio signals 547. The user device on which the stethoscope module 500 runs may have received an analog diagnostic audio signal and converted the analog diagnostic audio signal into a digital diagnostic audio signal 547. The diagnostic audio signals 547 may be received as one or more compressed or uncompressed audio files, which may have been generated by the user device. For example, one or more waveform (WAV) audio files, audio interchange file format (AIFF) audio files, AU audio files, or other uncompressed audio files may be received. Examples of lossless compression audio file formats that may be used for the digital audio signals 547 include free lossless audio codec (FLAC), true audio (TTA), Apple lossless (m4a), Windows media audio lossless (WMA lossless), and so on. Examples of lossy compression audio file formats include an MP3 audio file format, Vorbis, advanced audio coding (AAC), OGG, and so on.

In one embodiment, a digital audio signal includes one or more audio files that have been placed into a ring buffer. Stethoscope module 500 may retrieve the digital audio file(s) from the ring buffer on a periodic basis as the ring buffer becomes full. In one embodiment, the ring buffer holds 2 seconds of audio data. Alternatively, the ring buffer may hold 1 second, 3 seconds, 4 seconds, or some other amount of audio data. In one embodiment, a size of the ring buffer is equal to a sample period used for processing the audio data.

One or more filters 510 are used to filter the received diagnostic audio signals 547. The filters 510 may include a band pass filter, a notch filter, a down sampling filter and/or other filters. Each of the filters may be implemented by a processing device. In one embodiment, a filter selection module 560 determines which filters to apply to the received diagnostic audio signals 547. The determination of which filters 510 to use may be based on multiple factors. Such factors may include a type of medical information that is to be determined from the diagnostic audio signals 547 (e.g., whether a patient's heartbeat is to be analyzed or a patient's breathing is to be analyzed), a geographic location of the electronic stethoscope and/or the user device, a frequency used for the audio signature 547, and/or other factors.

In one embodiment, filter selection module 560 determines a geographic location of the user device running stethoscope module 500. The geographic location may be determined using a global positioning system (GPS) receiver of the user device, based on triangulation with multiple cell towers of a wireless carrier, and/or based on a home location setting of the user device. Different countries use different alternating current (AC) power supply frequency standards. For example, the United States uses a frequency of 60 Hz to supply AC power, and European countries and Japan use a frequency of 50 Hz to supply AC power. The AC power supply may cause background noise at the frequency of the AC power supply. This background noise may be picked up by the electronic stethoscope. Accordingly, filter selection module 560 may determine an AC power supply frequency associated with the location of the user device, and then enable a filter to filter out the diagnostic audio signals 547 at that frequency. For example, a notch filter that filters out the audio signal at 50 Hz may be applied in Europe, and a notch filter that filters out the audio signal at 60 Hz may be applied in the United States.

As previously mentioned, pairing module 555 may periodically or continuously send an audio signature 546 to the electronic stethoscope and/or the electronic stethoscope may periodically or continuously send an audio signature to the user device on which stethoscope module 500 executes.

These audio signatures 546 may be included in the received diagnostic audio signals 547, but are not based on sounds produced by a patient's body. Accordingly, filter selection module 560 may determine what frequency is used for the audio signature 546 (e.g., 2 kHz, 10 kHz, or other frequency), and may enable a filter to filter out that frequency from the diagnostic audio signatures 547.

In one embodiment, a band pass filter is used to filter the diagnostic audio signal 547. The band pass filter may pass signals having a frequency range of 50 Hz to 250 Hz in one embodiment. In one embodiment, a low pass filter is used to filter the diagnostic audio signal 547. The low pass filter may pass frequencies at around 500 Hz. For example, a 500 Hz low pass filter with a Q coefficient of 5 may be used to pass frequencies of about 495-505 Hz.

In one embodiment, a down sampling filter such as a decimation filter may be used to down sample the already filtered diagnostic audio signal 547. The down sampling filter may be applied after the application of one or more band pass and/or notch filters (e.g., that filter out the audio signatures 546, that filter out the AC power supply frequency, etc.) In one embodiment, the down sampling filter down samples the diagnostic audio signal by at least 50%. In a further embodiment, the down sampling filter down samples the diagnostic audio signal from 44 KHz to 8 KHz. Down sampling may be performed to reduce an amount of data to be processed. This may speed up further processing of the diagnostic audio signal 547.

Filter selection module 560 may additionally select filters to apply based on whether the neonate heart rate module 570, the adult/child heart rate module 575 or the breathing module 580 is to process the diagnostic audio signals. Infants have a much higher heart beat than adults and older children. Additionally, different frequencies may be important for detecting breathing information than for detecting heart beat information. Accordingly, a first filter or set of filters may be applied if a neonate's heart beat is to be detected and a second filter or set of filters may be applied if an adult or child's heart beat is to be detected, for example. Similarly, a third filter or set of filters may be applied if a patient's breathing is to be detected.

In one embodiment, the type of patient medical information to be determined (and which sub-module 570, 575, 580 to use) is not initially known. Accordingly, filter selection module 560 may apply a first set of filters and provide first filtered diagnostic audio signals to neonate heart rate module 570, and may in parallel apply a second set of filters and provide second filtered diagnostic audio signals to adult/child heart rate module 575 and apply a third set of filters and provide third filtered diagnostic audio signals to breathing module 580. Each of these sub-modules 570, 575, 580 may separately process their respective received diagnostic audio signals, and compare the processed diagnostic audio signals to stored models. The sub-module that produces a processed diagnostic audio signal that most closely matches a stored model may be selected for processing the diagnostic audio signals 547. Alternatively, a user may input a type of data to be gathered and/or information about a patient. An appropriate sub-module 570, 575, 580 may then be selected based on the user input.

Noise determiner 525 processes the filtered digital audio signal to determine a signal to noise ratio (SNR). Noise determiner may then compare the SNR to a threshold. If the SNR is above a threshold, then noise determiner 525 may determine that the data can be trusted. If the SNR is below the threshold, then noise determiner 525 may determine that the digital audio signal 545 has too much noise to be trusted.

Filtered and/or unfiltered diagnostic audio signals may be recorded for later playback.

Neonate heart rate module 570 determines the heart rate and/or other neonate medical information from diagnostic audio signals. The first few minutes of life after birth is a critical time when dramatic physiologic changes take place to prepare an infant for the outside world. Often, some term and many premature neonates are born with complications that require immediate resuscitation to survive. The neonate heart rate is one of the key physiologic metrics doctors use for determining whether or not a resuscitation effort is working. Because the infant's heart rate is so important, an accurate, instantaneous representation of the heart rate can be useful. Conventional neonate heart rate detection methods use manual palpation of the pulsating umbilical cord or listening to (auscultation) with a stethoscope for heartbeats, both of which are prone to inaccuracy and human error, particularly in situations of high stress and in the presence of external stimuli or noises. Furthermore, these methods complicate the delivery room working area by increasing the number of bodies. Conventional pulse oximetry and electrocardiograms also suffer from disadvantages due to respective signal delay (between 1 and 3 minutes) or difficulty with application. Neonate heart rate module may capture and report the neonate heart rate immediately and accurately to a resuscitation team after birth and provide real time audio and visual feedback. This may improve the quality of resuscitation offered and help critical time sensitive decisions to be made.

Neonate heart rate module 570 computes a heart rate from the filtered digital diagnostic audio signal 547. To compute the heart rate, neonate heart rate module 570 may first determine a mean value over a sample period. The sample period may be a 1 second window, a 2 second window, a 4 second window, a 6 second window, or other window. The sample period may be a moving window in one embodiment. In such an embodiment, the mean value may be a moving (or rolling) average. Once the mean is calculated, neonate heart rate module 570 identifies all peaks that are above the mean. Neonate heart rate module 570 may identify each such peak as a heartbeat. Neonate heart rate module 570 may then compute the interval between the beats, and use this interval to determine the heart rate. In one embodiment, the heart rate is computed as an average of the intervals between heart beats.

Neonate heart rate module 570 may compare the calculated heart rate to a heart rate threshold (e.g., to a neonate heart rate threshold of 100 beats per minute). If the heart rate is below the heart rate threshold, then neonate heart rate module 570 may output a warning. This warning may indicate that a neonate is likely to need resuscitation.

Adult/child heart rate module 575 may process the filtered digital diagnostic audio signal 547 in the same manner as described above with reference to the neonate heart rate module 570, but may apply different thresholds. For example, adult/child heart rate module 575 may compare the calculated heart rate to a heart rate threshold of 60 beats per minute or another value. If the heart rate is below the heart rate threshold, then adult/child heart rate module 575 may output a warning. The types of warnings output by adult/child heart rate module 575 may differ from those of neonate heart rate module 570 in some embodiments. For example, neonate heart rate module 570 may recommend resuscitation, while adult/child heart rate module 575 may recommend seeing a doctor.

Breathing module 580 may process the filtered digital diagnostic audio signal 547 to compute a patient respiratory rate and/or a patient inspiratory to expiratory ratio. Breathing module 580 may first determine a mean amplitude of the audio data collected over a sample period. The sample period may be a 1 second window, a 2 second window, a 4 second window, a 6 second window, or other window. The sample period may be a moving window in one embodiment. In such an embodiment, the mean value (mean amplitude) may be a moving (or rolling) average. Once the mean is calculated, breathing module 580 identifies the time period of sounds with frequencies between 50-400 Hz corresponding to normal vesicular breath sounds that are above the mean. In one embodiment, periods of sounds with absence of frequencies between 50-400 Hz are identified as periods of apnea. Breathing module 580 may then compute the interval between the normal vesicular breath sounds and periods of apnea, and use this interval to determine the respiratory rate. Inspiratory and expiratory phases of respiration may be calculated by means of the start of the apnea phase marking the end of a previous respiratory phase and the end of the apnea phase marking the start of a new respiratory phase. Inspiratory to expiratory ratio may be calculated by determining the mean difference of expiratory and inspiratory time periods.

User interface 530 may be a graphical user interface that may output the calculated heart rate. What is displayed by the user interface 530 may depend on which of the sub-modules 570, 575, 580 is running and/or based on what type of medical information is being determined. One example user interface for the neonate heart rate module 570 and/or adult/child heart rate module 575 is shown below in FIG. 12.

In one embodiment, the user interface 530 displays a numerical value for a heart rate. This numerical value may be shown with a first graphical indicator if the heart rate is below a heart rate threshold and may be shown with a second graphical indicator if the heart rate is above a heart rate threshold. Additionally, different graphical indicators may be displayed depending on whether the diagnostic audio signal 547 has an SNR that is above an SNR threshold. For example, the heart rate can be shown inside of a yellow heart if the SNR is too low and inside of a green heart if the SNR is sufficient.

The user interface 530 may also generate an audio output (e.g., a beep or other noise) at a rate to correspond to the heart rate. For example, if the heart rate is 130 beats per minute, then the user interface 530 may output a beep 130 times per minute. In one embodiment, the sound that is output changes based on at least one of the computed SNR or the computed heart rate. For example, a first sound may be output if the heart rate is within a healthy tolerance, and a second sound may be output if the heart rate is outside of the healthy tolerance (e.g., too high or too low).

The user interface 530 may also cause the user device to vibrate at the determined rate. In one embodiment a filtered signal trace of the digital audio signal is also displayed in the user interface 530.

The user interface 530 may additionally show a user where to place the electronic stethoscope on a patient (e.g., where on the back or chest to place the electronic stethoscope). If multiple readings are to be taken, the user interface 530 may guide a user through placement of the electronic stethoscope at a series of locations on a patient's body. User interface 530 may also prompt a user to input a patient activity state (e.g., whether the patient was recently exercising, is resting, is laying down, etc.).

Once medical data is generated, user interface 530 may display the medical data. The medical data may be displayed alone, together with past medical data of the same patient, or together with medical data of others. For example, a patient's heartbeat may be displayed on a heartbeat chart to show how the patient's heart rate compares to a general population.

In one embodiment, the stethoscope module 500 includes a projection module 585 that establishes a connection to an additional computing device. The additional computing device may be a tablet computer, smart television, desktop computer, laptop computer, mobile phone, wearable computer (e.g., Google Glass), and so on. The connection may be established via Bluetooth, Zigbee, Wi-Fi, or other wireless communication protocol. In one embodiment, the projection module 585 creates a socket server that connects via Wi-Fi to the additional computing device.

Once the connection to the additional computing device is established, projection module 585 transmits (e.g., streams) information such as heart rate data or breathing data to the additional computing device. In one embodiment new data is transmitted every second, though other transmission frequencies may also be used. The additional computing device then displays the information (e.g., the heart rate in a heart icon of an appropriate color).

FIGS. 6-10 are flow diagrams illustrating methods of interfacing with an electronic stethoscope and of generating medical information from a diagnostic audio signal from the electronic stethoscope. These methods may be performed, for example, to monitor an infant heart rate or an adult heart rate using an electronic stethoscope coupled to a user device having a stethoscope module installed thereon. These methods may be performed by processing logic that may include hardware (e.g., circuitry, dedicated logic, programmable logic, microcode, etc.), software (such as instructions run on a processing device, a general purpose computer system, or a dedicated machine), firmware, or a combination thereof. The methods may be performed by a user device, such as user device 400 of FIG. 4.

For simplicity of explanation, the methods are depicted and described as a series of acts. However, acts in accordance with this disclosure can occur in various orders and/or concurrently and with other acts not presented and described herein. Furthermore, not all illustrated acts may be performed to implement the methods in accordance with the disclosed subject matter. In addition, those skilled in the art will understand and appreciate that the methods could alternatively be represented as a series of interrelated states via a state diagram or events.

Figure 6:
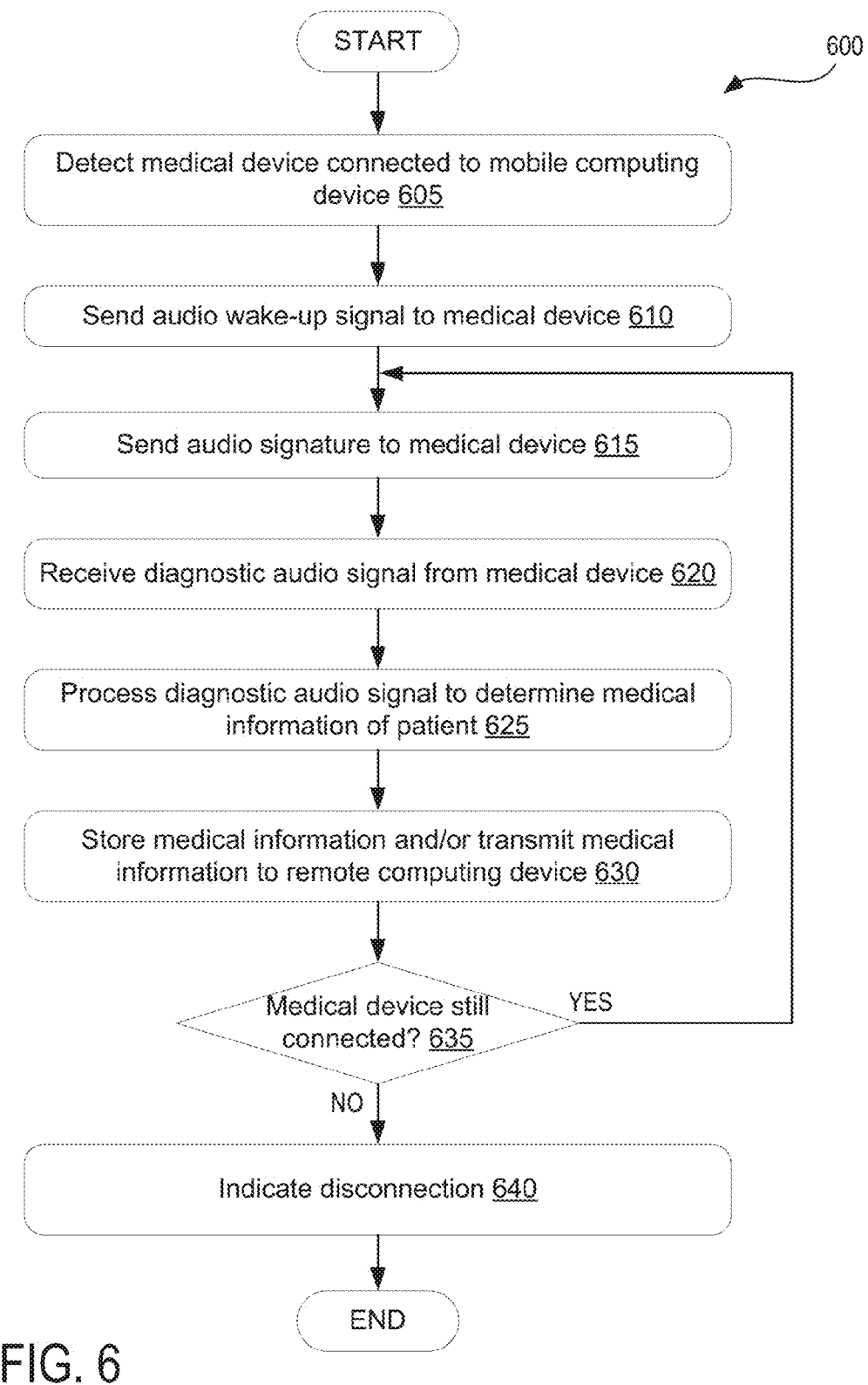
FIG. 6 is a flow diagram illustrating one embodiment for a method of activating an electronic stethoscope and receiving and processing a diagnostic audio signal from the electronic stethoscope.

FIG. 6 is a flow diagram illustrating one embodiment for a method 600 of activating an electronic stethoscope or other medical device and receiving and processing a diagnostic audio signal from the electronic stethoscope or other medical device. At block 605 of method 600, processing logic detects a medical device connected to a mobile computing device or other user device. In one embodiment, the detected medical device is an electronic stethoscope. The medical device may be detected by receiving an audio signal or other signal from the medical device once the mobile computing device has connected to the medical device. Alternatively, processing logic may treat any connected device as a medical device.

At block 610, processing logic sends an audio wake-up signal to the medical device. The audio wake-up signal may be sent to the device before the device is identified as a medical device in some embodiments. The audio wake-up signal may have a particular tone, frequency, loudness, etc. that the medical device waits for. In such an embodiment, the wake-up signal may cause the medical device to transition from a low power state to a higher power state (e.g., may have activated). In one embodiment, the medical device responds to the wake-up signal with a confirmation signal after being activated. The confirmation signal may identify the device as a medical device. The confirmation signal in one embodiment is an audio signature that processing logic may use to identify and/or authenticate the medical device. Alternatively, the medical device may not send any response after being activated.

At block 615, processing logic sends an audio signature to the medical device. The medical device uses the audio signature to authenticate the mobile computing device. If the mobile computing device is authenticated, the medical device will begin generating a diagnostic audio signal and transmitting that diagnostic audio signal to the mobile computing device.

At block 620, processing logic receives the diagnostic audio signal. In one embodiment, the diagnostic audio signal is an analog audio signal. The analog audio signal may be received through a stereo port of the mobile computing device (e.g., via a 3.5 mm stereo port common on mobile phones).

At block 625, processing logic processes the diagnostic audio signal to determine medical information of a patient. Processing the diagnostic audio signal may include converting an analog audio signal into a digital audio signal, filtering the digital audio signal using software and/or hardware filters, and analyzing the filtered audio signal to determine medical information such as a heart rate, strength of heart beat, breathing information, and so on. Examples of breathing information that may be determined include identification of rales (small clicking, bubbling or rattling sounds in lungs heard while a patient breathes in), rhonci (sounds that resemble snoring caused by blockage of airflow through the large airways), stridor (a wheeze-like sound usually caused by blockage of airflow in the trachea or back of throat), wheezing (high pitch sound produced by narrowed airways), and so on. At block 630, processing logic stores the medical information and/or transmits the medical information to a remote computing device for storage and/or further analysis. Processing logic may also store the diagnostic audio signal for future playback.

At block 635, processing logic determines whether the medical device is still connected. This determination may be made based on whether an updated diagnostic audio signal is received, and/or based on whether an audio signature was received. While the medical device is connected, the medical device should continuously or periodically output a diagnostic audio signal until it receives a signal to stop measuring from the mobile computing device. If no diagnostic signal has been received for a threshold amount of time (e.g., 0.5 seconds, 1 second, 5 seconds, etc.), then processing logic may determine that the medical device has been disconnected from the mobile computing device. If the medical device is still connected, then the method may return to block 615, at which processing logic again sends the audio signature to the medical device. Processing logic may continuously or periodically send the audio signature to the medical device to keep the medical device from transitioning to a low power state.

If the medical device has been disconnected, the method continues to block 640, and processing logic outputs a message indicating that the medical device has been disconnected from the mobile computing device. This may include an audio message and/or a display of a text or graphical message, for example. The method may then end.

Figure 7:
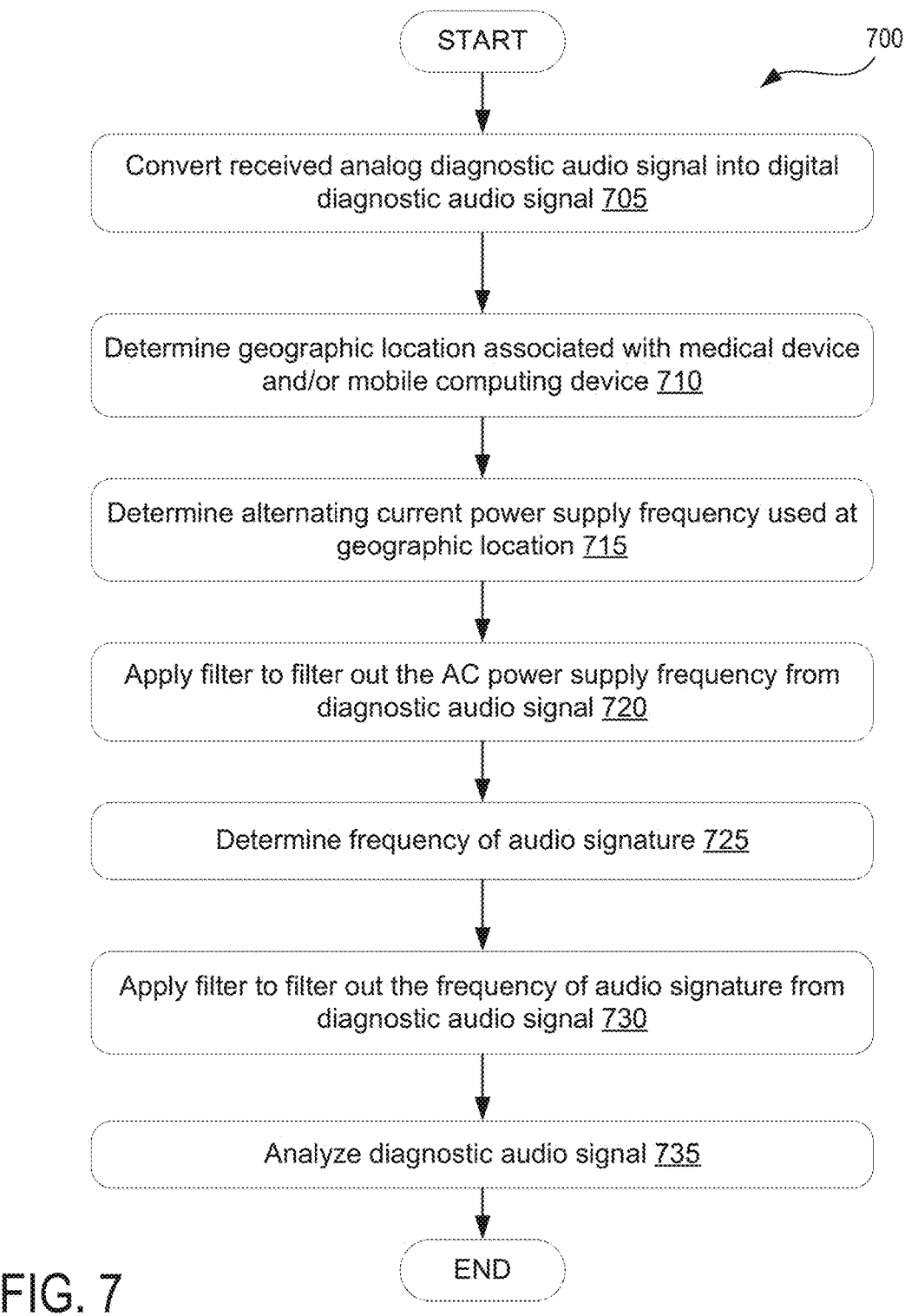
FIG. 7 is a flow diagram illustrating one embodiment for a method of processing a diagnostic audio signal received from an electronic stethoscope.

FIG. 7 is a flow diagram illustrating one embodiment for a method 705 of processing a diagnostic audio signal received from an electronic stethoscope or other medical device. In one embodiment, method 705 is performed at block 625 of method 600. At block 705 of method 700, processing logic converts a received analog diagnostic audio signal into a digital diagnostic audio signal. At block 710, processing logic determines a geographic location associated with a mobile computing device that includes the processing logic and/or a geographic location associated with a medical device (e.g., an electronic stethoscope) connected to the mobile computing device. The location of the mobile computing device may be determined using location services included in the mobile computing device. The location services may determine the location of the mobile computing device using a GPS receiver of the mobile computing device, using triangulation of the mobile computing device to multiple cell towers or Wi-Fi access points, and/or using a home location of the mobile computing device. The location of the medical device may be determined to be the same as the location of the mobile computing device in one embodiment.

At block 715, processing logic determines an alternating current (AC) power supply frequency used at the geographic location. At block 720, processing logic applies a filter to filter out the AC power supply frequency from the diagnostic audio signal.

At block 725, processing logic determines a frequency of an audio signature that is used to authenticate the mobile computing device to the medical device and/or that is used to authenticate the medical device to the mobile computing device. At block 730, processing logic applies a filter to filter out the frequency of the audio signature from the diagnostic audio signal.

Processing logic may also apply additional filters, such as a down sampling filter. The down sampling filter may reduce the amount of data that is processed to analyze the diagnostic audio signal.

At block 735, processing logic analyzes the diagnostic audio signal. Analyzing the diagnostic audio signal may include identifying waveform patterns in the diagnostic audio signal. Based on the analysis, processing logic may determine a heart rate of a patient, strength of the patient's heart beat, breathing information of the patient, and/or other medical information of the patient.

Figure 8:
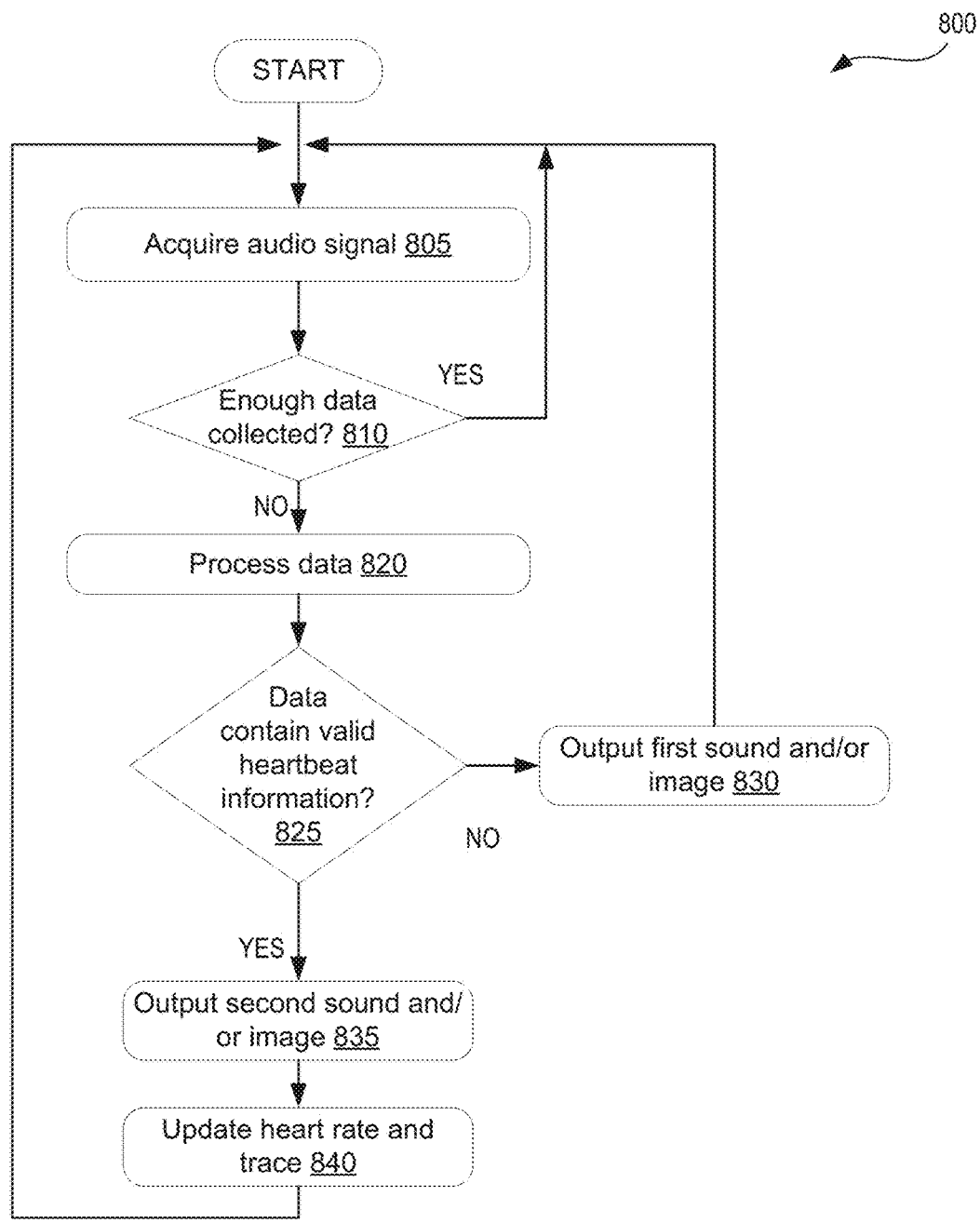
FIG. 8 is a flow diagram illustrating another embodiment for a method of processing a diagnostic audio signal received from an electronic stethoscope.

FIG. 8 is a flow diagram illustrating another embodiment for a method 800 of processing a diagnostic audio signal received from an electronic stethoscope by a user device such as a mobile computing device that has a stethoscope module installed thereon. Method 800 may be performed by processing logic executing a neonate heart rate module or an adult/child heart rate module of a stethoscope module. Method 800 may be performed together with methods 600 and/or 700 in some embodiments.

At block 805 of method 800, processing logic acquires an audio signal. At block 810, processing logic determines whether enough data has been collected (e.g., whether a ring buffer has been filled). If not enough audio data has been collected, the method returns to block 805 and additional audio data is collected. If enough data has been collected, the method proceeds to block 820.

At block 820, processing logic processes the acquired audio data to determine the heart rate information in the collected audio data. At block 825, processing logic determines whether the collected audio data contains valid heartbeat information. The collected audio data contains valid heartbeat information if block 820 returns a list of detected heartbeat per minute (BPM) results from the analysis of the collected data. If the no valid heartbeat information is detected in the collected audio data, the method proceeds to block 830 and a first image and/or sound may be output. For example, an image of a red heart may be displayed. The computed heart rate may or may not be shown inside of the image of the red heart. If valid heartbeat information is detected, then the method continues to block 835, and a second image and/or sound is output. For example, an image of a green heart may be shown. At block 840, processing logic further displays the heart rate in the second image (e.g., in the image of the green heart). Additionally, processing logic may output a beating heart sound (or other sound) at a rate corresponding to the heart rate. Processing logic may also display a filtered signal trace of the audio signal for the heartbeat. In one embodiment, the analysis of the audio signal produces a calculated mean heart rate over 5 seconds, a signal to noise ratio that is updated every 20 milliseconds and an amplitude trace updated every 20 milliseconds. The method may return to block 805 to continue to acquire and process a diagnostic audio signal.

Figure 9:
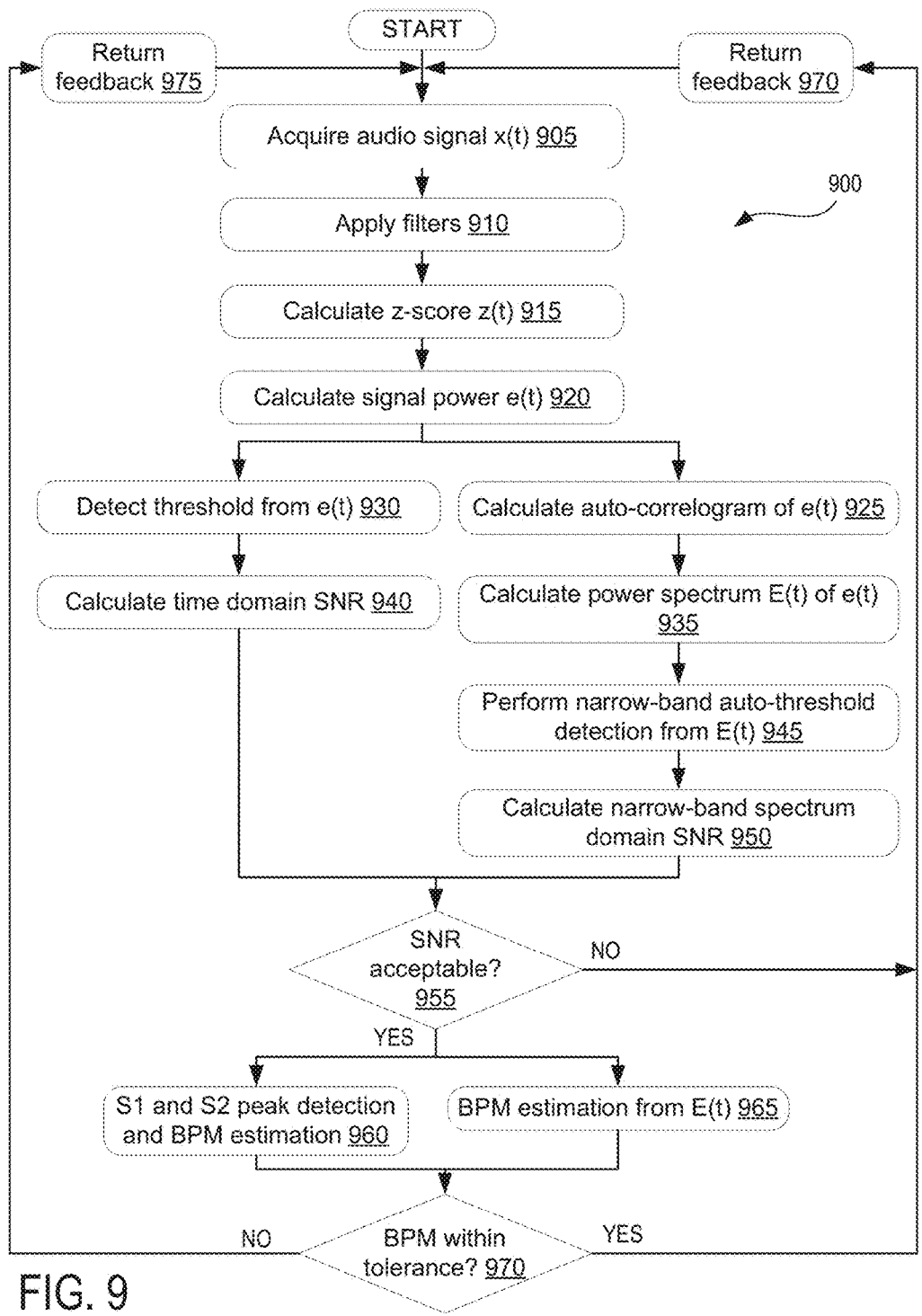
FIG. 9 is a flow diagram illustrating another embodiment for a method of processing a diagnostic audio signal received from an electronic stethoscope.

FIG. 9 is a flow diagram illustrating another embodiment for a method 900 of processing a diagnostic audio signal received from an electronic stethoscope. In one embodiment, method 900 is performed to determine a heart rate of a patient. At block 905 of method 900, an audio signal x(t) is received. At block 910, the audio data is filtered by applying any one or more of the filters described herein above. At block 915, a z-score z(t) is computed from the audio data x(t), as shown below:

$$z(t) = \frac{x(t) - \operatorname{mean}(x(t))}{\operatorname{std}(x(t))} \quad (1)$$

where mean(x(t)) is the average value of the audio signal x(t), and std(x(t)) is the standard deviation of the audio signal x(t).

At block 920, a signal power e(t) is computed from the z-score by taking a squared value of the z-score:

$$e(t) = z(t)^2 \quad (2)$$

Operations are then performed in subsequent blocks to calculate multiple different SNRs. At block 930, a threshold is calculated by multiplying the mean of the signal power e(t) by a value determined empirically to place the threshold between the noise floor and the peak values of the signal power e(t) if the data contains heart beats. In one embodiment, a value of 10 is adequate for signals containing adult heart beats, which has peak values of 5 z-score and hence 25 in signal power. The noise floor of such signals typically has a noise floor or 1 z-score. The threshold would then be positioned at 5 to be between the noise floor and the peak values. At block 940, processing logic computes a time-domain SNR by running a peak detection algorithm with the calculated threshold. The time domain SNR may be based on the number of peaks detected above the threshold within a time window (e.g., within a time window of 3 seconds). The SNR may be acceptable in one embodiment if more than 2 peaks are detected above the threshold and are spaced reasonably on the time axis (e.g. the time elapsed between peaks indicates a realistic beat per minute value in human, which is between 30 bpm to 200 bpm). The method proceeds to block 955.

In parallel to the operations of block 930, at block 925 processing logic calculates an auto-correlogram of the signal power e(t) by calculating the cross correlation of e(t). At block 935, processing logic calculates a power spectrum E(t) of the calculated signal power e(t) by calculating the Fourier Transformation of E(t). At block 945, processing logic detects a threshold from the power spectrum E(t) by calculating the mean of the power spectrum density of E(t), and multiplying it by an empirically determined value (e.g. 0.5) that places the threshold between the peak values and 0 over the range on the power spectrum density that corresponds to the human heart activities (i.e. 0.5 Hz to 3.3 Hz). At block 950, processing logic calculates a narrow-band spectrum-domain SNR by calculating the number of peak values above the threshold on the power spectrum density over the range of interest. The SNR may be acceptable in one embodiment if 1 to 3 peaks are detected. The method then continues to block 955.

At block 955, processing logic determines whether the signal SNR value or values are acceptable. The signal SNRs may be acceptable if both the calculated SNRs are acceptable. If the SNR values are acceptable, the method continues to blocks 960 and 965. Otherwise, the method proceeds to block 970, at which feedback is returned, and after which the method returns to block 905. The feedback may include a message (e.g., an error message) that is output by the mobile computing device.

At blocks 960 and 965, processing logic takes the previously computed peak values above the thresholds (as described above), and then converts them to BPM (beat per minute) values. At block 960, a time domain based method is used on the peaks obtained in block 940, where the elapsed time between peaks is used to calculate the BPM. In one embodiment, if the time elapsed between two large peaks is 0.8 seconds, this implies a heartbeat frequency of $$\frac{1}{0.8} = 1.25 \text{ Hz},$$

the BPM value is hence 1.25*60=75 BPM. At block 965, a frequency domain based method is used on the peaks obtained in block 950, where the position of the peak on the spectrum density plot indicates the BPM. In one embodiment, if a large peak is present on the spectrum density plot at 1.5 Hz, this indicates the BPM is 1.5*60=90 BPM.

At block 970, processing logic takes the intersection of the BPMs calculated in 960 and 965, and calculates the mean of intersection. Processing logic then determines whether the estimated beats per minute (BPM) is within a tolerance (e.g., above a minimum threshold and/or below a maximum threshold). The threshold may be based on the age of the patient whose heartbeat is being measured. For example, a threshold of 100 BPM may be used for a neonate, while a threshold of 60 BPM may be used for an adult. If the BPM is within tolerance, then the heart rate may be a healthy heart rate and the method continues to block 975, at which feedback is provided. The feedback may include the heart rate, a signal trace, a message, etc. The method then returns to block 905. If the estimated BPM is not within the tolerance, then the heart rate may be a potentially unhealthy heart rate and the method continues to block 970, and feedback is returned. The feedback may include the heart rate, a signal trace, a message, an alarm, etc. The method then returns to block 905.

Figure 10:
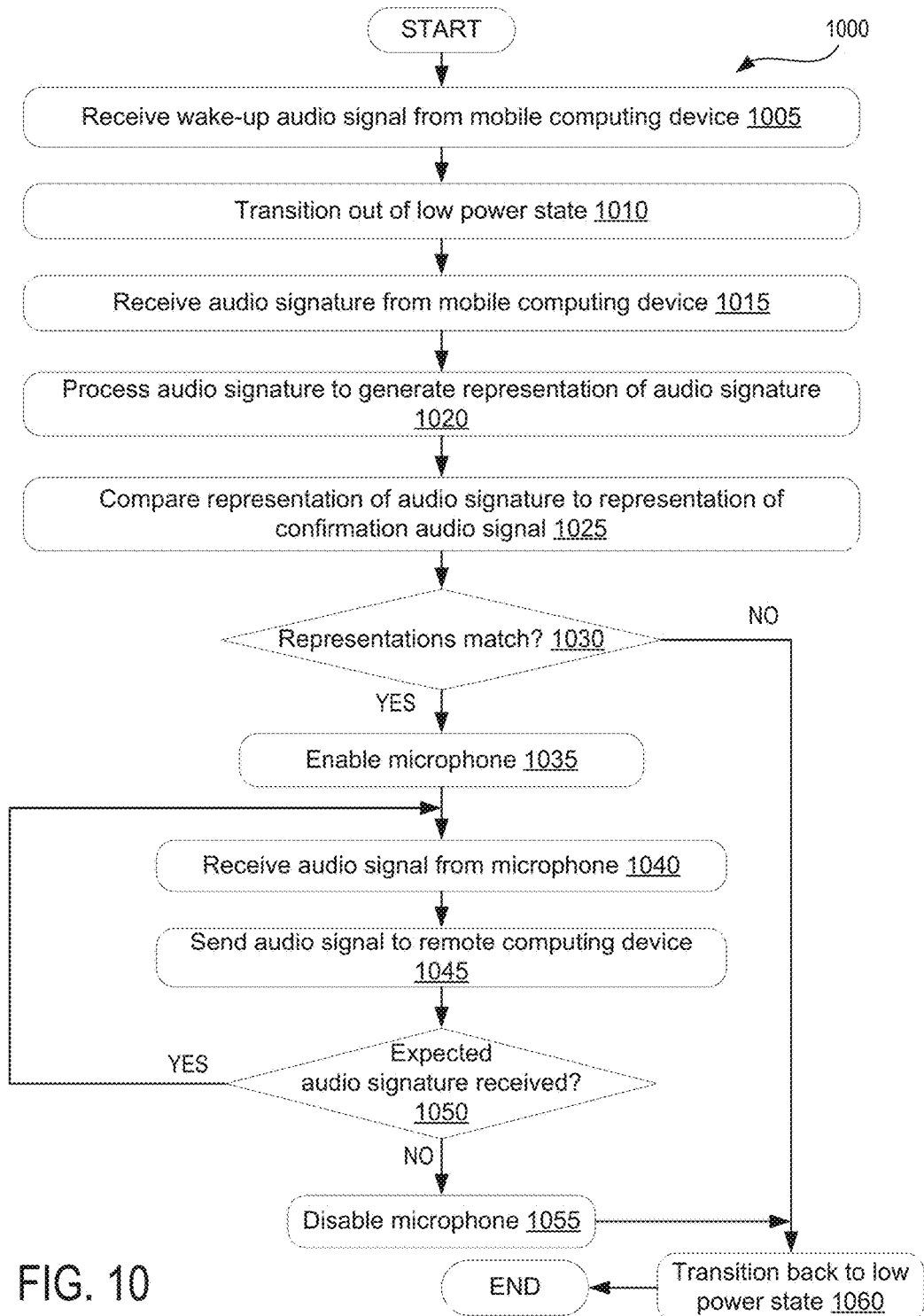
FIG. 10 is a flow diagram illustrating one embodiment for a method of operating an electronic stethoscope.

FIG. 10 is a flow diagram illustrating one embodiment for a method 1000 of operating an electronic stethoscope. Method 1000 may be performed by an electronic stethoscope, such as by electronic stethoscope attachment 105 of FIGS. 1A-1E and/or electronic stethoscope 200 of FIGS.

2-3. At block 1005 of method 1000, processing logic of the electronic stethoscope receives a wake-up audio signal from a mobile computing device executing a stethoscope module (e.g., a stethoscope application). The electronic stethoscope may be in a low power or standby mode when the wake-up signal is received. At block 1010, the electronic stethoscope transitions out of the low power state. This may include activating modules/logics of a processing device of the electronic stethoscope.

At block 1015, processing logic of the electronic stethoscope receives an audio signature from the mobile computing device. At block 1020, processing logic processes the audio signature to generate a representation of the audio signature. Processing the audio signature may include performing a Fourier transform (e.g., a fast Fourier transform) on the audio signature. At block 10225, processing logic compares the representation to a representation of a confirmation audio signal. The confirmation audio signal may be stored in memory of the electronic stethoscope, and processing logic may generate the representation of the confirmation audio signal for the comparison. Alternatively, the representation of the confirmation audio signal may be stored.

At block 1030, processing logic determines whether the representations match. If the representations match, the method continues to block 1035. Otherwise, the method proceeds to block 1060.

At block 1035, processing logic enables a microphone of the electronic stethoscope. This may include coupling the microphone to a power source and/or coupling the microphone to a port of the electronic stethoscope. At block 1040, processing logic receives an audio signal from the microphone. At block 1045, processing logic sends the audio signal to a remote computing device via the port. Alternatively, the microphone may send the audio signal directly to the remote computing device via the port.

The remote computing device may continually or periodically send the audio signature to the electronic stethoscope while connected to the electronic stethoscope. At block 1050, processing logic determines whether an expected audio signature was received. If an expected audio signature is not received, the method proceeds to block 1055. If the expected audio signature is received, the method returns to block 1040. In one embodiment, processing logic resets a timer each time an audio signature is received. If a new audio signature is not received before the timer times out, the method continues to block 1055. The timer may have a time period of 0.5 seconds, 1 second, 5 seconds, or some other time period. The timer period may be based on the frequency with which the audio signature is received. For example, the time period may be 1 times the frequency, 2 times the frequency, 3 times the frequency, and so on. In an example using a time period of 2 times the frequency, if two consecutive expected audio signatures are not received, the method continues to block 1055.

At block 1055, the microphone is disabled. This may include disconnecting the microphone from a power source and/or disconnecting the microphone from the port. At block 1060, the electronic stethoscope transitions back to the low power state. While in the low power state, the processing logic then monitors the port for a new wake-up audio signature.

Figure 11:
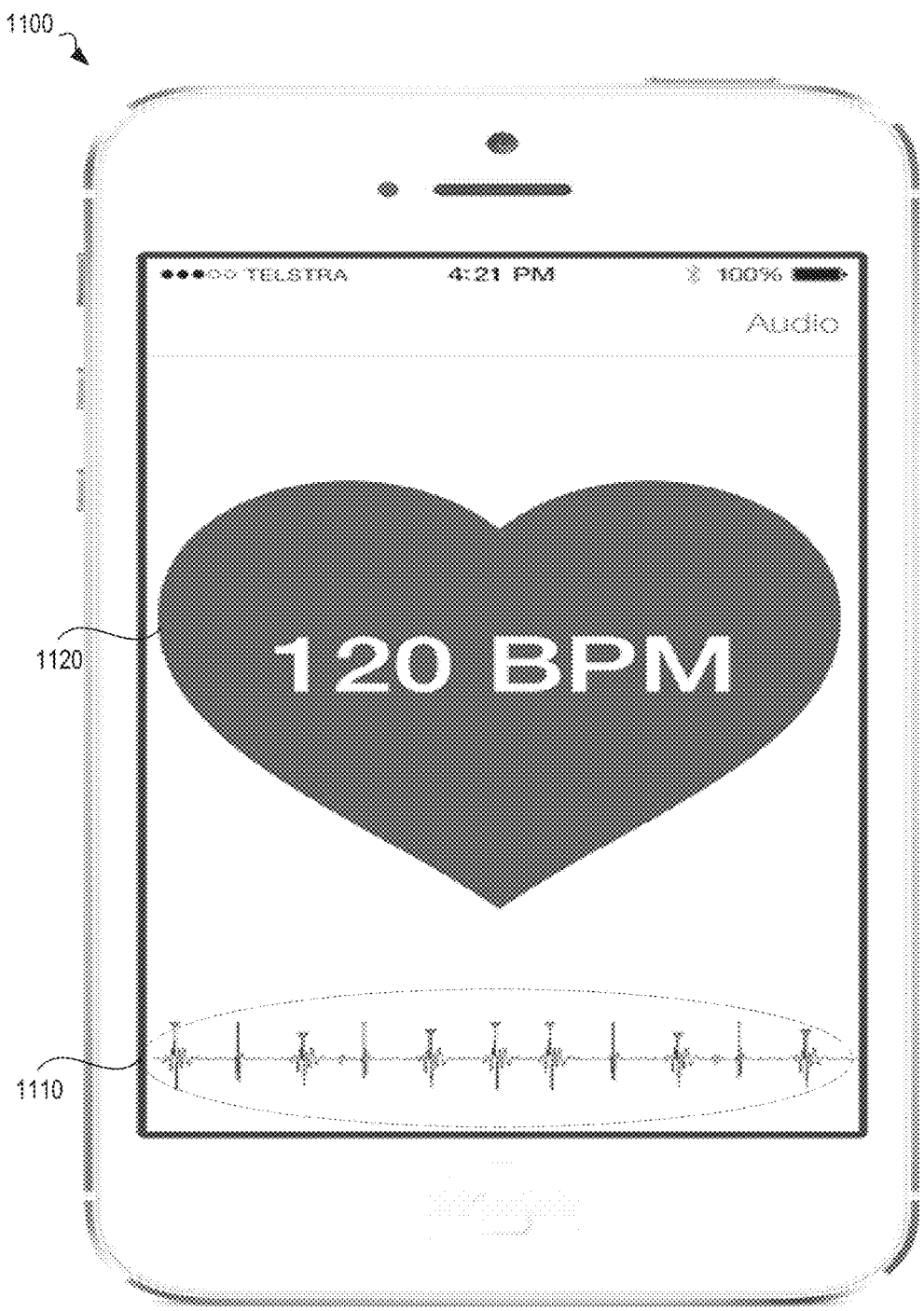
FIG. 11 is a user interface of a stethoscope module, in accordance with one embodiment.

FIG. 11 is a user interface 1100 of a stethoscope module, in accordance with one embodiment. As shown, the user interface displays a heart rate value 1120 within a color coded heart icon. The heart graphic may be green if a SNR ratio is adequate (at or above a threshold) and may be yellow if the SNR value is not adequate (below the threshold). The icon may change to red if no signal is present or if the signal strength is of unreliable quality. Other color schemes may also be used. Additionally, the color may change based on whether the measured heart rate is within a healthy heart rate range for a patient (e.g., above 100 for a neonate). The user interface 1100 may additionally include a filtered signal trace 1110 of the patient's heart beat.

In the above description, numerous details are set forth. It will be apparent, however, to one of ordinary skill in the art having the benefit of this disclosure, that embodiments may be practiced without these specific details. In some instances, well-known structures and devices are shown in block diagram form, rather than in detail, in order to avoid obscuring the description.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like. The blocks described herein can be hardware, software, firmware, or a combination thereof.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "detecting," "filtering," "determining," "processing," "converting," "receiving," "displaying," or the like, refer to the actions and processes of a computing system, or similar electronic computing device, that manipulates and transforms data represented as physical (e.g., electronic) quantities within the computing system's registers and memories into other data similarly represented as physical quantities within the computing system memories or registers or other such information storage, transmission or display devices.

Use of the term "an embodiment" or "one embodiment" or "an implementation" or "one implementation" throughout this application is not intended to mean the same embodiment or implementation unless described as such. Also, the terms "first," "second," "third," "fourth," etc. as used herein are meant as labels to distinguish among different elements and may not necessarily have an ordinal meaning according to their numerical designation.

Embodiments descried herein may also relate to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer-readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, flash memory, or any type of media suitable for storing electronic instructions. The term "computer-readable storage medium" should be taken to include a single medium or multiple media (e.g., a centralized or distributed database and/or associated caches and servers) that store the one or more sets of instructions. The term "computer-readable medium" shall also be taken to include any medium that is capable of storing, encoding or carrying a set of instructions for execution by the machine and that causes the machine to perform any one or more of the methodologies of the present embodiments. The term "computer-readable storage medium" shall accordingly be taken to include, but not be limited to, solid-state memories, optical media, magnetic media, or any other non-transitory medium that is capable of storing a set of instructions for execution by the machine and that causes the machine to perform any one or more of the methodologies of the present embodiments.

The above description sets forth numerous specific details such as examples of specific systems, components, methods and so forth, in order to provide a good understanding of several embodiments. It will be apparent to one skilled in the art, however, that at least some embodiments may be practiced without these specific details. In other instances, well-known components or methods are not described in detail or are presented in simple block diagram format in order to avoid unnecessarily obscuring the present embodiments. Thus, the specific details set forth above are merely exemplary. Particular implementations may vary from these exemplary details and still be contemplated to be within the scope of the present embodiments.

It is to be understood that the above description is intended to be illustrative and not restrictive. Many other embodiments will be apparent to those of skill in the art upon reading and understanding the above description. The scope of the present embodiments should, therefore, be determined with reference to the appended claims, along with the full scope of equivalents to which such claims are entitled.

What is claimed is:

1. An electronic stethoscope comprising:
   a body;
   a diaphragm at one end of the body;
   a microphone housed within the body; and
   a processing device housed within the body and connected to the microphone, wherein the processing device is configured to:
     receive a first audio signal from a computing device connected to the electronic stethoscope via a connection; and
     enable the microphone responsive to receipt of the first audio signal, wherein the microphone is to generate a second analog audio signal based on sound waves amplified by the diaphragm, and wherein the second audio signal is transmitted to the computing device.

2. The electronic stethoscope of claim 1, further comprising:
   a memory coupled to the processing device, wherein the memory is configured to store at least one of a confirmation audio signal or a representation of the confirmation audio signal;
   wherein the first audio signal comprises an audio signature, and wherein the processing device is further configured to:
     determine whether a representation of the audio signature matches the representation of the confirmation audio signal; and
     enable the microphone responsive to determining that the representation of the first audio signal matches the representation of the confirmation audio signal.

3. The electronic stethoscope of claim 2, wherein the processing device is further configured to:
   periodically or continuously receive the audio signature while the electronic stethoscope is connected to the computing device; and
   disable the microphone responsive to a determination that the audio signature has not been received within a time period.

4. The electronic stethoscope of claim 3, wherein the processing device is further configured to:
   transmit a message to the computing device responsive to disabling the microphone, wherein the message indicates the electronic stethoscope has been disconnected from the computing device.

5. The electronic stethoscope of claim 2, wherein the connection comprises a wired connection to a 4-pole stereo plug of the computing device.

6. The electronic stethoscope of claim 5, further comprising:
   a cable that provides the wired connection to the 4-pole stereo plug of the computing device, wherein the cable comprises a universal serial bus (USB) connector at a first end and a 3.5 mm stereo connector at a second end, and wherein the cable is configured to transmit analog audio signals from the computing device to the electronic stethoscope and from the electronic stethoscope to the computing device.

7. The electronic stethoscope of claim 5, wherein the wired connection to the 4-pole stereo plug of the computing device powers the electronic stethoscope.

8. The electronic stethoscope of claim 1, wherein the processing device is further configured to:
   receive an audio wake-up signal before receiving the first audio signal; and
   transition out of a low power state responsive to receipt of the audio wake-up signal.

9. The electronic stethoscope of claim 1, further comprising a ring coupled to the diaphragm at one end of the body.

10. The electronic stethoscope of claim 1, wherein the processing device is further configured to:
    transition to a low power state responsive to the microphone being powered off for a threshold amount of time.

11. The electronic stethoscope of claim 1, wherein the processing device is further configured to process the second analog audio signal to determine medical information of a patient.

12. The electronic stethoscope of claim 1, further comprising a memory coupled to the processing device, wherein the memory is configured to store the second analog audio signal for a playback of the second analog audio signal.

* * * * *